US00PP08708P

United States Patent [19]

Voth et al.

[11] Patent Number: Plant 8,708

[45] Date of Patent: May 3, 1994

[54] STRAWBERRY PLANT CALLED 'CAMAROSA'

[75] Inventors: Victor Voth, Santa Ana; Douglas V. Shaw; Royce S. Bringhurst, both of Davis, all of Calif.

[73] Assignee: The Regents of the University of California, Oakland, Calif.

[21] Appl. No.: 41,742

[22] Filed: Apr. 1, 1993

[51] Int. Cl.[5] ..... A01H 5/00

[52] U.S. Cl. ..... Plt./49

[58] Field of Search ..... Plt. 48, 49

*Primary Examiner*—James R. Feyrer

*Attorney, Agent, or Firm*—Townsend and Townsend Khourie and Crew

[57] ABSTRACT

'Camarosa' is a short-day (June bearing) cultivar similar to 'Chandler' (U.S. Plant Pat. No. 5,262) but with greater total productivity, substantially greater early productivitiy, larger fruit, firmer fruit, and is a more vigorous plant.

2 Drawing Sheets

DESCRIPTION

This invention relates to a new and distinctive short-day type cultivar designated as 'Camarosa', which resulted from a cross performed in 1988 between the cultivar 'Douglas' (U.S. Plant Pat. No. 4,487) and advanced selection Cal 85.218-605.

'Camarosa' was first fruited at the University of California South Coast Research and Extension Center, near Irvine, Calif. in 1989, where it was selected, originally designated Cal 88.24-603, and propagated asexually by runners. Asexual propagules from this original source have been tested at the South Coast Research and Extension Center, the Watsonville Strawberry Research Facility, and to a limited extent in grower fields starting in 1990.

Figure 1:
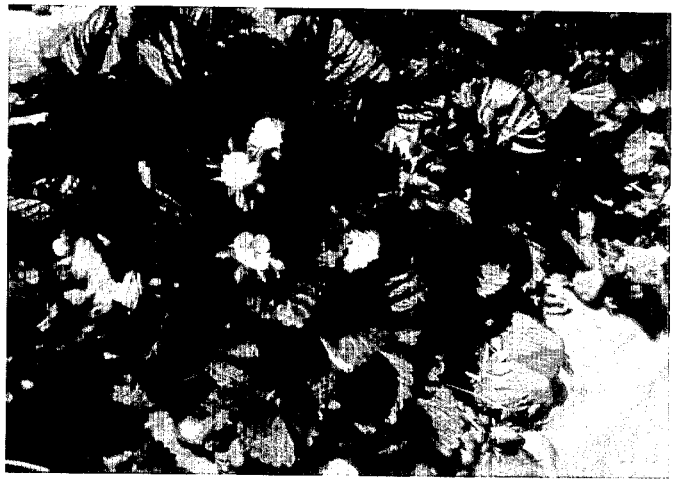
FIG. 1 shows the general flowering and fruiting characteristics of the plant.
Figure 2:
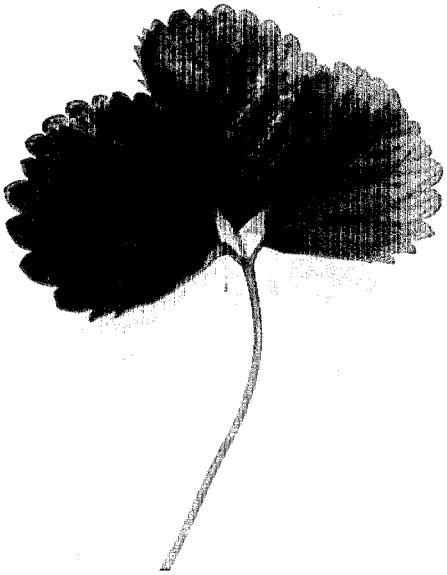
FIG. 2 shows a typical mature leaf during late spring.
Figure 3:
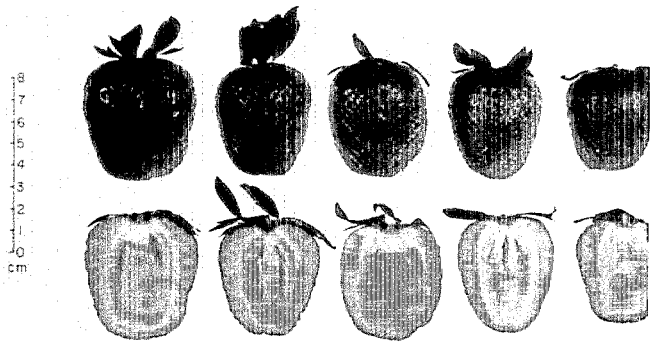
FIG. 3 shows representative mid-season fruit.

'Camarosa' is typical of short-day types and produces fruit over an extended period when treated appropriately in arid, subtropical climates. 'Camarosa' has a substantially greater yield than 'Douglas' and greater fruit firmness. The production pattern for 'Camarosa' is similar to that for 'Chandler' (U.S. Plant Pat. No. 5,262), although it produces substantially greater quantities of early-season fruit. 'Camarosa' will be of special interest for winter plantings, where 'Chandler' has been successful, and in summer plantings where 'Pajaro' (U.S. Plant Pat. No. 4,538) has been successful.

Plants and Foliage

Fruiting plants of 'Camarosa' are larger, more erect, and more vigorous than plants of 'Chandler', and are generally similar in form to plants of 'Oso Grande' (U.S. Plant Pat. No. 6,578). 'Camarosa' forms branch crowns in greater quantity than 'Chandler' with similar branching to 'Oso Grande'. When propagated in the nursery, 'Camarosa' has similar or greater runner production capacity compared with 'Chandler'. Comparative statistics for foliar characters, including leaf color, near mid-season are given for the three cultivars in Table 1, with visual comparisons of leaf color to the Munsell color scale (Nickerson Color Fan) given in Table 5. Leaf color is distinctly lighter on the underside for 'Camarosa'; the differential is similar to that for 'Chandler' and not as large as for 'Oso Grande'. Individual leaflets for 'Camarosa' are larger, somewhat longer and more narrow than for 'Chandler', and are less rounded than for 'Oso Grande'. Leaves (including petioles) are similar in length to 'Chandler', but are much broader. Petioles are thicker and more stiff than those of 'Chandler' and are similar to those of 'Oso Grande'. Paired stipules, borne in a median position on the petiole, appear as small, stalked, ovate to heart-shaped structures on some leaves for 'Camarosa' and on most leaves for the comparison cultivars. Stipule size varies greatly both within and among individual plants for 'Camarosa', and one or both stipules are frequently absent or may abscise as the leaf matures. Leaf and petiole pubescence characters for 'Camarosa' are similar to those for 'Oso Grande', except that tomentum on leaves are less dense. Also, leaves for 'Camarosa' are similar in reflectance to 'Chandler' but darker green (less yellow), and similar in color intensity to 'Oso Grande'. Visual comparisons of fruit color according to the Munsell color scale (Nickerson Color Fan) are given in Table 5. 'Camarosa' has concave leaves; less concave than leaves of 'Chandler', and similar to those of 'Oso Grande'.

Isozymes in Leaf Extracts

'Camarosa' has been classified for three isozyme systems using starch gel electrophoresis (Table 2): Phosophoglucoisomerase (PGI), Leucine Aminopeptidase (LAP), and Phosphoglucomutase (PGM). It is distinguishable from all other short-day cultivars released to date. For electrophoretic procedures see: J. Amer. Soc. Hort. Sci. 106:684–687.

Disease and Pest Reaction

'Camarosa' is moderately susceptible to common leaf spot (*Ramularia tulasnei*) and relatively resistant to powdery mildew (*Sphaerotheca macularis*). When treated properly, it has equal or greater tolerance to two-spotted spidermites (*Tetranychus urticae*) than 'Chandler'. 'Camarosa' is tolerant to strawberry viruses encountered in California.

TABLE 1

Foliar characteristics for 'Camarosa', 'Chandler', and 'Oso Grande'.

| Foliar Character | Cultivar 'Camarosa' | 'Chandler' | 'Oso Grande' |
|---|---|---|---|
| Mid-tier leaflet | | | |
| Length (mm) | | | |
| mean | 97.4 | 82.4 | 77.2 |
| range | 80–117 | 78–94 | 75–80 |
| Width (mm) | | | |
| mean | 79.8 | 71.4 | 67.6 |
| range | 70–92 | 63–88 | 62–71 |
| Mid-tier leaf | | | |
| Length (mm) | | | |
| mean | 234.2 | 244.2 | 191.6 |
| range | 210–253 | 218–262 | 170–200 |
| Width (mm) | | | |
| mean | 143.6 | 148.0 | 137.2 |
| range | 135–180 | 132–158 | 130–149 |
| Leaf color (CIELAB)* | | | |
| L* | | | |
| mean | 31.5 | 31.4 | 31.9 |
| range | 28.4–34.5 | 27.1–33.3 | 29.9–33.0 |
| a* | | | |
| mean | −5.9 | −8.0 | −5.3 |
| range | −3.1–−9.4 | −5.2–−8.2 | −4.2–−8.3 |
| b* | | | |
| mean | 14.0 | 16.0 | 15.5 |
| range | 11.1–20.7 | 12.9–21.4 | 12.5–20.6 |
| # leaflets/leaf | 3 | 3 | 3 |
| Leaf convexity | concave | concave | concave |
| Serrations | | | |
| number | few | many | moderate |
| shape | semi-round | semi-pointed | semi-round |
| Leaf pubescence | moderate | moderate/ sparse | moderate/ heavy |
| Petiole pubescence | | | |
| density | heavy | heavy | heavy |
| direction | perpendicular | acropetal | perpendicular |

*CIELAB is the abbreviation of the international color system known as "Commission Internationale De L'Eclairage" 1978. Recommendations on uniform color spaces -- color difference equations, psychometric color terms. Supplement No. 2 to CIE Publication No. 15. PARIS.

TABLE 2

Isozyme phenotypes for 'Camarosa', 'Chandler', and 'Oso Grande'.

| Locus | Cultivar 'Camarosa' | 'Chandler' | 'Oso Grande' |
|---|---|---|---|
| PGI | A2 | A1 | A2 |
| LAP | B3 | B3 | B3 |
| PGM | C1 | C1 | C2 |

Flowering, Fruiting, Fruit, and Production Characteristics

Comparative statistics for flower and fruit characters, including fruit color, near mid-season are given for the three cultivars in Table 3. The primary flowers for 'Camarosa' are similar in size to 'Chandler' and 'Oso Grande', whereas the sepals are somewhat larger than for the comparison cultivars. The calyx for 'Camarosa' varies from slightly indented to slightly necked, and each primary flower has 5–6 petals. The fruit shape for 'Camarosa' can vary but is typically a very flat conic, and is easily distinguished from 'Chandler' (flat conic, with some long conic) and 'Oso Grande' (rounded or blocky conic). External fruit color for 'Camarosa' is similar to 'Chandler' and 'Oso Grande,' and the fruit is at least as glossy as 'Chandler'; internal color is darker than for 'Chandler' and substantially darker than for 'Oso Grande'. Achenes vary from light red to dark red, and are even with the fruit surface or slightly indented.

'Camarosa' has been tested under a variety of cultural regimes, and optimal performance is obtained when nursery treatments, preplant chilling regimes, plant densities, and nutritional programs similar to those that optimize performance for 'Chandler' are used. In general, 'Camarosa' is more adapted to early-season planting with less supplemental chilling than 'Chandler'.

When treated with appropriate planting regimes, 'Camarosa' has larger fruit and produces greater yields than 'Chandler' (Table 4); 'Camarosa' has greater yield but smaller fruit than 'Oso Grande'. 'Camarosa' is similar to 'Chandler' and 'Oso Grande' in its production pattern, although it produces substantially more early-season fruit than either comparison cultivar (with conventional winter planting). Commercial appearance ratings have been comparable to or better than those for 'Chandler'. Fruit for 'Camarosa' is substantially firmer than fruit from 'Chandler'; 'Camarosa' is about as firm as 'Oso Grande'. Subjectively, 'Camarosa' has very good flavor, somewhat less aromatic than 'Chandler', but with better acid balance and more aromatic components than 'Oso Grande'. The fruit will be outstanding for both fresh market and processing, due to its firm flesh and very dark internal color, and will be useful for home garden purposes.

TABLE 3

Flower and fruit characters for 'Camarosa', 'Chandler', and 'Oso Grande'.

| Character | Cultivar 'Camarosa' | 'Chandler' | 'Oso Grande' |
|---|---|---|---|
| # petals | | | |
| mean | 6.3 | 6.6 | 5.0 |
| range | 5–7 | 6–8 | 5–5 |
| Flower position (relative to foliage) | even/ exposed | even/ exposed | exposed |
| Calyx diam. (mm) | | | |
| mean | 57.1 | 47.7 | 34.1 |
| range | 50–63 | 45–53 | 27–38 |
| Corolla diam. (mm) | | | |
| mean | 39.3 | 39.3 | 32.2 |
| range | 35–42 | 36–46 | 27–41 |
| Fruit shape | | | |
| length/width ratio | 1.13 | 1.33 | 1.06 |
| subjective | flat/ some conic | flat conic | blocky/conic |
| Calyx position | even/slight indent | even/slight neck | even/slight indent |
| Seed position | even/slight indent | even/slight indent | even |
| Fruit color (CIELAB) | | | |
| external | | | |
| L* | 23.1 | 23.6 | 22.4 |
| a* | 29.7 | 38.5 | 31.2 |
| b* | 16.6 | 14.8 | 17.2 |
| internal | | | |
| L* | 43.6 | 46.2 | 54.1 |
| a* | 40.8 | 39.1 | 30.4 |
| b* | 30.9 | 29.4 | 22.7 |

TABLE 4

Performance for selection 'Camarosa' compared with 'Oso Grande' and 'Chandler' at the South Coast Research and Extension Center in 1991. All plants were dug from the South Coast nursery on October 1 and planted October 2 (68"/4-row beds, 23,061 plants/A, 100 g/plant = 425 Crates/A).

| | Yield To 4/1 (g/plant) | Total Yield (g/plant) | Size (g/fruit) | Appearance Score | Firmness |
|---|---|---|---|---|---|
| 'Camarosa' | 555 | 2,380 | 24.6 | 4.4 | 4.7 |
| 'Chandler' | 463 | 1,738 | 23.3 | 3.9 | 4.0 |
| 'Oso Grande' | 530 | 1,675 | 25.0 | 3.8 | 4.9 |

TABLE 5

Munsell color classification for leaf and fruit characters.

| | Munsell Leaf Color Classes | | Munsell Fruit Color Classes | |
|---|---|---|---|---|
| Item | Upper (Adaxial) | Lower (Abaxial) | External | Internal |
| Chandler | 5GY 4/3<br>5GY 5/6 | 5GY 5/6 | 5R 5/13<br>5R 4/12 | 7R 5/13 |
| Oso | 5GY 4/3<br>5GY 3/2 | 5GY 5/6<br>7.5GY 6/8 | 5R 5/13<br>7.5R 5/13 | 7.5R 7/9<br>7.5R 6/12 |
| Camarosa | 5GY 4/3 | 5GY 5/6 | 7.5R 4/11<br>7.5R 3/6 | 7.5R 5/13<br>7.5R 4/11 |

We claim:

1. The new and distinct variety of strawberry plant illustrated and described and having the characteristics above enumerated.

* * * * *